United States Patent [19]
Ardaillon et al.

[11] Patent Number: 4,877,621
[45] Date of Patent: Oct. 31, 1989

[54] COMPOSITIONS FOR COATING FEEDSTUFF ADDITIVES FOR RUMINANTS AND FEEDSTUFF ADDITIVES THUS COATED

[75] Inventors: Pierre Ardaillon, Saint-Priest; Pierre Autant, Commentry; Paul Bourrain, Dardilly; Andre Cartillier, Commentry, all of France

[73] Assignee: Rhone-Poulenc Sante, Courbevoie, France

[21] Appl. No.: 92,139

[22] Filed: Sep. 2, 1987

[30] Foreign Application Priority Data

Sep. 4, 1986 [FR] France .............................. 86 12412

[51] Int. Cl.$^4$ .............................................. A61K 9/16
[52] U.S. Cl. ..................................... 424/498; 424/438
[58] Field of Search ......................................... 424/438

[56] References Cited

U.S. PATENT DOCUMENTS

| T100,404 | 3/1981 | Wu ....................................... | 424/482 |
| 4,196,187 | 4/1980 | Dannelly et al. .................... | 424/489 |
| 4,675,175 | 6/1987 | Autant et al. ....................... | 424/438 |

FOREIGN PATENT DOCUMENTS

| 2838278 | 3/1979 | Fed. Rep. of Germany ...... | 424/438 |
| 2160096 | 12/1985 | United Kingdom . | |

*Primary Examiner*—Ferris H. Lander
*Assistant Examiner*—Anthony J. Green
*Attorney, Agent, or Firm*—Stevens, Davis, Miller & Mosher

[57] ABSTRACT

A composition for coating a biologically active substance, which is stable in a medium with a pH greater than or equal to 5 and which enables the active substance to be released in a medium with a pH less than or equal to 3.5, consisting of a basic amino copolymer (preferably vinyl-pyridine/styrene copolymer) and a hydrophobic substance with a melting point greater than 60° C. (preferably stearic acid), the hydrophobic substance content being between 50 and 90% of the total mass of the coating, and granules comprising a nucleous containing the biologically active substance, coated with this composition.

9 Claims, No Drawings

COMPOSITIONS FOR COATING FEEDSTUFF ADDITIVES FOR RUMINANTS AND FEEDSTUFF ADDITIVES THUS COATED

The present invention relates to compositions for coating feedstuff additives intended for ruminants, which are stable in a medium with a pH equal to or greater than 5.5 and which enable the feedstuff additive to be released in a medium with pH less than or equal to 3.5.

When certain biologically active substances (medicinal products, vitamins, amino acids) are administered to ruminants, enzymatic destruction of these substances, promoted by the residence time (from a few hours to several days) and by the pH (between 5 and 6), occurs during their passage through the rumen. As a result, the active substance, which is degraded, has lost the major part of its efficacy by the time it reaches the abomasum.

Therefore, it is important to be able to protect these biologically active substances with coatings which are stable in the rumen of ruminants, ie which are stable against degradation by microorganisms and which enable the biologically active substance to be released in a part of the digestive system, more particularly in the abomasum, the pH of which is less than or equal to 3.5. While the period of protection in the rumen must be relatively long (from a few hours to several days), the release of the active substance in the abomasum must occur in a relatively short period of time (from a few minutes to 1 or 2 hours).

Many coating compositions are known. French patent publication No. 2514261 describes a coating which consists of a copolymer which is sensitive to pH variations, which is a copolymer of styrene with one or more vinyl pyridine, and a water-insoluble polymer which is insensitive to pH variations, which is cellulose acetobutyrate, ethyl cellulose or cellulose propionate. This polymer promotes the release of the active substance at a pH of between 1 and 2.5 and decreases the extractability of the active substance in an aqueous medium. However, although such coatings give satisfactory results with methionine, they lead to poorer results with lysine, whose properties are significantly different from those of methionine, especially water solubility.

French patent publication No. 2401620 proposes coating feedstuffs for ruminants with a styrene-vinyl pyridine copolymer containing a hydrophobic substance which is a fatty acid containing 10 to 32 carbon atoms or polycarboxylic acid containing 10 to 22 carbon atoms per carboxyl group, which improves the protection by decreasing the overall susceptibility of the film coating to aqueous media which are slightly acid in nature. In these compositions, the hydrophobic substance is present in the coating in an amount of 5 to 75% of the mass of the polymer substance. In the active substance granules thus coated, the coating represents 5 to 50% of the mass of the granules. The coated granules generally have a diameter of between 1.2 and 19 mm. In order to improve the properties of the coated granules, it is possible to add flaky fillers such as aluminium powder, talcum or mica to the coating composition.

In these compositions, the concentration of basic amino copolymer remains very high. Moreover, the coating composition appears to be truly effective only in the case of granules of a relatively large size, in which the coating layer is relatively thick (approximately 150 microns).

In the case where flaky fillers are introduced, technological problems of implementation may be encountered, especially in the spray-coating technique.

The present invention provides a composition suitable for coating a biologically active substance for ruminants, the said composition being stable in a medium with a pH greater than or equal to 5 and enabling the biologically active substance to be released in a medium with a pH less than 3.5, which comprises a basic amino copolymer and a hydrophobic substance which has a melting point greater than 60° C., the hydrophobic substance content being from 50 to 90% of the total mass of the coating.

The hydrophobic substance with a melting point greater than 60° C. is a fatty acid, fatty ester or fatty alcohol or mixture thereof.

Apart from the important difference in behaviour at pH=6 and at pH=2 this coating composition has the advantage of having a lower toxicity because the quantity of basic amino copolymer that it contains is low. Additionally, this composition has an excellent resistance to degradation during storage (attrition and agglomeration) and to biological degradation due to moulds.

The basic amino copolymer of the coating composition is a copolymer of styrene with one or more vinylpyridine such as 2-vinyl-pyridine, 4-vinylpyridine or 2-methyl-5-vinylpyridine. In general, the nitrogen content in the basic amino copolymer is from 3 to 14%.

The hydrophobic substance with a melting point greater than 60° C. is preferably stearic acid or behenic acid. Stearic acid with a purity greater than 90% is of very particular value.

The hydrophobic substance of the composition, which is present in large excess relative to the basic copolymer, ensures a good retention at pH=6 and the basic copolymer binds together the crystals of the hydrophobic substance. The binder, which is distributed uniformly in the thickness of the coating, is destroyed in an acid medium, under the action of protons, thereby causing a destruction of the cohesiveness of the membrane, with a quick release of the active substance.

Apart from the basic copolymer and the hydrophobic substance, the coating composition may contain adjuvants whose role is to facilitate the implementation of the techniques for the preparation of the composition or to improve the physicochemical properties. It may be advantageous to employ plasticizers (e.g. triacetin and propylene glycol), antistatic agents (e.g. triglycerides containing ethylene oxide-polycondensate chains), fungicidal agents, emulsifiers (e.g. polycondensates of ethylene oxide with sorbitan esters, and sugar glycerides), compatibility-inducing agents (e.g. natural or seminatural gums such as polysaccharides such as alginates, tragacanth gum, pectins, carraghenates, and xanthan gum), cellulose ehters (e.g. carboxymethyl-, methyl- and hydroxypropylcellulose) or fillers such as inorganic salts, sugar, starch or proteins. In general, these various adjuvants represent only a few percent (e.g. 3%) by weight of the coating composition.

The composition may be obtained by dispersing or dissolving the basic copolymer in a solution or a suspension of the hydrophobic substance in an organic solvent or in a mixture of suitable organic solvents chosen depending on the specific nature of the constituents. The coating composition is generally obtained after evaporating off the solvent(s). An alcohol (e.g. ethanol), an ether (e.g. tetrahydrofuran), a ketone (e.g. acetone) or a chlorinated aliphatic solvent (e.g. methylene chloride or 1,2-dichloroethane) or a mixture of these solvents is generally employed as the organic solvent. It is particularly advantageous to employ an ethanol/1,2-dichloroethane mixture, an ethanol/methylene chloride mixture, an ethanol/acetone mixture or an ethanol/tetrahydrofuran mixture.

The coating composition is particularly useful for protecting various therapeutic or nutrient substances such as medicinal products such as nitroxynil, peptide or polypeptide hormones, vitamins such as vitamin A or amino acids such as methionine and lysine, intended for oral administration to ruminants. These coated substances are generally mixed with the animal feed.

The coating composition is particularly suitable for coating methionine and lysine.

The coated substance is preferably granular in the form of microcapsules consisting of a central nucleus surrounded by a continuous film of the coating composition. However, the active substance may also be dispersed in the coating composition. In general, the coating composition represents 5 to 50% by weight of the granule or the dispersion.

The present invention also relates to biologically active substances which are coated or dispersed in a coating composition described above.

The granules may be obtained by applying known techniques. Depending on the nature of the coating composition, techniques involving extrusion or spraying of solutions or of emulsions in fluidized beds, or techniques involving encapsulation in a molten or semi-molten medium, or techniques involving coating in a liquid medium, such as coacervation, are employed.

The granules obtained are stable during storage and handling, do not deteriorate during the preparation of animal feed stuffs and are not destroyed during their absorption by animals and, in particular, by crushing or by grinding when they are chewed. In order to increase the resistance of the granules during storage at relatively high temperatures (60° C.) and more particularly in order to prevent the grains from sticking to each other, it is advantageous to carry out a film-coating, for example with zein or with hydroxypropylmethylcellulose.

The size of the granules will depend on the use they are intended for and, more particularly, it will be determined according to the animals they are intended for. The granules of the active substance to be coated generally have a diameter of between 0.1 and 5 mm.

In order to obtain a satisfactory result, it is generally sufficient that the thickness of the film coating is in the vicinity of 50 microns, irrespective of the granule size. As a result, the content of coating material decreases with increasing initial size of the granule. Thus, if the active substance granules to be coated have a mean diameter of 0.55 mm, the coating material content will be in the vicinity of 35% whereas if the granules to be coated have a mean diameter of 1.1 mm, the coating material content will be in the vicinity of 20%. Increasing the initial diameter of the granules increases the active substance content in the coated granule and decreases the basic polymer:active substance ratio, which represents significant advantages from an economical point of view as well as from a nutritional point of view.

In order to demonstrate the sensitivity of these coating compositions to pH variations, tests to determine the rate of release active substance with time were carried out at different pH values and especially at pH=6 and at pH=2.

For example, the rate of release of active substance present in the granules is studied by stirring, under defined conditions, a known quantity of granules in a buffered medium at constant pH, at a temperature of 40° C. The rates of release in a sample are compared at different pH values and more particularly at pH=6 and at pH=2.

The following examples illustrate the coating compositions according to the present invention and their use in the preparation of coated active substances.

EXAMPLE 1

According to the fluidized bed technique with a vessel equipped with a WURSTER system, methionine (350 g), which has previously been granulated in the form of spherical particles with a concentration of 98%, the mean diameter of which is between 0.5 and 0.63 mm, is coated with a solution of the following composition:

stearic acid (m.p.=68°-69° C.; acid value=194-198): 88 g
2-vinylpyridine/styrene (70:30) copolymer: 22 g
1,2-dichloroethane: 500 cc
ethanol: 500 cc
antistatic agent (Labrasol, tradename GATTEFOSSE): 3 cc The viscosity of the 2-vinylpyridine/styrene (70:30) copolymer, determined at a concentration of 5 g/liter in dimethylformamide at 20° C. is 0.560. The viscosity is determined as the ratio $$\frac{T_1 - T_0}{T_0}$$

where $T_1$ is the flow time of the polymer solution and $T_0$ is the flow time of the solvent.

The solution, maintained at 27° C., is sprayed over 3 hours 40 min.

Coated granules (392 g), with a methionine content of 73% are thereby obtained.

The rate of release of methionine is determined by dispersing the granules (8 g) thus prepared in a buffered solution (1 Liter) maintained at 40° C. and stirred magnetically.

The quantity of methionine released is monitored in samples, the trials being carried out at pH=6 and at pH=2.

The results are collated in table 1.

EXAMPLE 2

The coating is carried out as in Example 1, but carrying out the spraying over 1 hour 30 min.

Granules (450 g) with a methionine content of 71.6% are thus obtained.

The results of trials on the rates of release are given in table 1.

EXAMPLE 3

The coating is carried out as in Example 1, but using a coating composition containing stearic acid (48.8 g) and 2-vinylpyridine/styrene (70:30) copolymer (12.2 g) and carrying out the spraying over 1 hour at 47° C.

Granules (400 g) with a methionine content of 82% are thus obtained.

The results of trials on the rates of release are given in table 1.

EXAMPLE 4

The coating is carried out as in Example 1, but using a coating composition containing stearic acid (40 g) and 2-vinylpyridine/styrene (70:30) copolymer (10 g) and carrying out the spraying over 45 minutes at 45° C.

Granules (381 g) with a methionine content of 86% are thus obtained.

The results of trials on the rates of release are given in table 1.

EXAMPLE 5

The coating is carried out as in Example 1, but replacing the 1,2-dichloroethane with methylene chloride.

The solution, maintained at 30° C., is sprayed over 44 minutes.

Granules (448 g) with a methionine content of 76.8% are thus obtained.

The results of trials on the rates of release are given in table 1.

EXAMPLE 6

Stearic acid (m.p.=66.9° C.; acid value=199; PRIFRAC acid marketed by UNICHEMA) (88 g) and 2-vinylpyridine/styrene (70:30) copolymer (22 g) are dissolved in methyl isobutyl ketone (80 g).

The solution is heated to 85° C. and it is added, over 8 minutes, to a solution containing water (990 cc) and 10% (w/v) sodium hydroxide (4.2 cc), which is stirred with a Polytron type of turbomixer. An emulsion which is fluid and homogeneous at a temperature greater than or equal to 54° C. is thus obtained.

According to the fluidized bed technique, with a vessel equipped with a WURSTER system, methionine (350 g) which has previously been granulated in the form of spherical particles, with a concentration of 98%, the mean diameter of which is between 0.5 and 0.63 mm, is coated with the emulsion obtained above.

The emulsion, maintained at 64° C., is sprayed over 59 minutes.

Coated granules (434 g) with a methionine content of 78% are thus obtained.

The results of trials on the rates of release are given in table 1.

EXAMPLE 7

The coating is carried out as in Example 6, but using an emulsion obtained by dispersing, at 85° C., a solution of stearic acid (88 g) and 2-vinylpyridine/styrene (70:30) copolymer (22 g) in methyl isobutyl ketone (80 g) in water (495 cc) and 10% (w/v) sodium hydroxide (4.2 cc).

The emulsion, maintained at 66° C., is sprayed over 33 minutes.

Coated granules (440 g) with a methionine content of 77.8% are thus obtained.

The results of trials on the rates of release are given in table 1.

EXAMPLE 8

The coating is carried out as in Example 6, but replacing the methyl isobutyl ketone (80 g) with butyl acetate (80 g).

The emulsion, maintained at 63° C., is sprayed over 65 minutes.

Coated granules (436 g) with a methionine content of 79% are thus obtained.

The results of trials on the rates of release are given in table 1.

TABLE 1

| Example | Methionine Content % | % Methionine released at pH = 6 after | | % Methionine released at pH = 2 after | | |
|---|---|---|---|---|---|---|
| | | 6h | 24h | 15 min | 30 min | 60 min |
| 1 | 72.9 | 1.3 | 2.9 | 82.0 | 84.0 | 100 |
| 2 | 71.0 | 1.5 | 3.2 | 86.0 | 89.0 | 100 |
| 3 | 82.0 | 3.9 | 8.3 | 100 | | |
| 4 | 86.0 | 5.6 | 14 | 99.0 | 99.0 | 100 |
| 5 | 76.8 | 1.2 | 3.0 | 100 | 100 | 100 |
| 6 | 78.0 | 1.5 | 2.4 | 100 | 100 | 100 |
| 7 | 77.8 | 1.7 | 3.0 | 100 | 100 | 100 |
| 8 | 79.0 | 2.4 | 5.2 | 100 | 100 | 100 |

EXAMPLE 9

The coating is carried out as in Example 1, but replacing the methionine with lysine hydrochloride (350 g) which has previously been granulated in the form of spherical particles, the mean diameter of which is between 0.63 and 0.80 mm and which has a concentration of 82%. The duration of spraying is 3 hours 30 min at 27°–30° C. Granules (450 g) with a lysine hydrochloride content of 60.0% are thus obtained.

The results of trials on the rates of release are given in table 2.

EXAMPLE 10

The coating is carried out as in Example 9, but using a coating composition containing stearic acid (93.5 g) and 2-vinylpyridine/styrene (70:30) copolymer (16.5 g) and carrying out the spraying over 3 hours 15 min. at 28°–30° C.

Granules (380 g) with a lysine hydrochloride content of 57.6% are thus obtained.

The results of trials on the rates of release are given in table 2.

EXAMPLE 11

The coating is carried out as in Example 9, but using a coating composition containing stearic acid (99 g) and 2-vinylpyridine/styrene (70:30) copolymer (11 g) and carrying out the spraying over 3 hours 15 min. at 29°–35° C.

Granules (445 g) with a lysine hydrochloride content of 60.2% are thus obtained.

The results of trials on the rates of release are given in table 2.

EXAMPLE 12

The coating is carried out as in Example 9, but using a coating composition containing stearic acid (77 g) and 2-vinylpyridine/styrene (70:30) copolymer (33 g) and carrying out the spraying over 1 hour 50 min. at 32°–40° C.

Granules (460 g) with a lysine hydrochloride content of 58.4% are thus obtained.

The results of trials on the rates of release are given in table 2.

EXAMPLE 13

The coating is carried out as in Example 9, but using a coating composition containing stearic acid (60.5 g)

and 2-vinylpyridine/styrene (70:30) copolymer (49.5 g) and carrying out the spraying over 2 hours 10 min. at 39°–41° C.

Granules (460 g) with a lysine hydrochloride content of 59.8% are thus obtained.

The results of trials on the rates of release are given in table 2.

EXAMPLE 14

The coating is carried out as in Example 9, but carrying out the spraying over 1 hour 30 min. at 37°–39° C.

Granules (445 g) with a lysine hydrochloride content of 61% are thus obtained.

The results of trials on the rates of release are given in table 2.

EXAMPLE 15

The coating is carried out as in Example 9, but using a solution of the coating composition in pure tetrahydrofuran and carrying out the spraying over 2 hours at 20° C.

Granules (457 g) with a lysine hydrochloride content of 60.7% are thus obtained.

The results of trials on the rates of release are given in table 2.

EXAMPLE 16

The coating is carried out as in Example 9, but using a solution of the coating composition in an ethanol:tetrahydrofuran (1:1 by volume) mixture and carrying out the spraying over 1 hour 40 min. at 20° C.

Granules (457 g) with a lysine hydrochloride content of 62% are thus obtained.

The results of trials on the rates of release are given in table 2.

EXAMPLE 17

The coating is carried out as in Example 9, but using a solution of the coating composition in an ethanol:acetone (1:1 by volume) mixture and carrying out the spraying over 3 hours 30 min. at 40° C.

Granules (455 g) with a lysine hydrochloride content of 59.2% are thus obtained.

The results of trials on the rates of release are given in table 2.

EXAMPLE 18

The coating is carried out as in Example 9, but replacing the stearic acid with behenic acid (docosanoic acid; m.p.=76° C.), the dichloroethane:ethanol mixture with a tetrahydrofuran:ethanol mixture and carrying out the spraying over 2 hours 40 min. at 56°–59° C.

Granules (445 g) with a lysine hydrochloride content of 59.2% are obtained.

The results of trials on the rates of release are given in table 2.

EXAMPLE 19

The coating is carried out as in Example 9, but using a coating composition which does not contain antistatic agent.

The solution, maintained at 35° C., is sprayed over 1 hour 40 minutes.

Coated granules (456 g) with a lysine hydrochloride content of 60% are thus obtained.

The results of trials on the rates of release are given in table 2.

EXAMPLE 20

A coating is carried out as in Example 9, but using a coating solution in which the 1,2-dichloroethane is replaced with the same quantity of methylene chloride.

The solution, maintained at 35° C., is sprayed over 42 minutes.

Coated granules (455 g) with a lysine hydrochloride content of 59% are thus obtained.

The results of trials on the rates of release are given in table 2.

EXAMPLE 21

An emulsion prepared as in Example 6 is employed for coating lysine hydrochloride (350 g) which has previously been granulated in the form of spherical particles the mean diameter of which is between 0.63 and 0.80 mm and which have a concentration of 82%.

The emulsion, maintained at 65° C., is sprayed over 64 minutes.

Coated granules (451 g) with a lysine hydrochloride content of 57% are thus obtained.

The results of trials on the rates of release are given in table 2.

EXAMPLE 22

(Comparative Example)

The coating is carried out as in Example 9, by using a coating composition consisting of technical grade stearic acid (93.5 g) and 2-vinylpyridine/styrene (70:30) copolymer (16.5 g).

Coated granules with a lysine hydrochloride content of 60.0% are thus obtained.

The results of trials on the rates of release are given in table 2.

The technical grade stearic acic employed, the melting point of which is 56° C., has the following composition: saturated fatty acids:
$C_{18}$: stearic acid: 44.1%
$C_{17}$: 2%
$C_{16}$: palmitic acid: 47%
$C_{14}$: myristic acid: 3%
$C_{12}$: lauric acid: traces
unsaturated fatty acids:

---
$C_{18}$: oleic acid
$C_{16}$: palmitoleic acid 4.5%
$C_{14}$: myristoleic acid
---

EXAMPLE 23

(Comparative Example)

The coating is carried out as in Example 9, by using a coating composition containing technical grade stearic acid (99 g) and 2-vinylpyridine/styrene copolymer (11 g).

Coated granules with a lysine hydrochloride content of 61.3% are thus obtained.

The results of trials on the rates of release are given in table 2.

It emerges from Examples 22 and 23 that the use of technical grade stearic acid does not enable a good retention to be achieved at pH=6 as compared, in particular, with the products of Examples 10 and 11.

TABLE 2

| Examples | Lysine hydrochloride content % | % Lysine hydrochloride released at pH = 6 after | | % Lysine hydrochloride released at pH = 2 after | | |
|---|---|---|---|---|---|---|
| | | 6h | 24h | 15 min | 30 min | 60 min |
| 9 | 60.0 | 6.0 | 15.6 | 98 | 98 | 100 |
| 10 | 57.6 | 5.0 | 13.0 | 100 | 100 | 100 |
| 11 | 60.2 | 23.0 | 37.0 | 100 | 100 | 100 |
| 12 | 58.4 | 6.5 | 14.0 | 100 | 100 | 100 |
| 13 | 59.8 | 9.3 | 16.6 | 97.0 | 97.0 | 99 |
| 14 | 61.0 | 6.0 | 11.5 | 100 | 100 | 100 |
| 15 | 60.7 | 13.7 | 28.3 | 100 | 100 | 100 |
| 16 | 62.0 | 8.0 | 17.0 | 100 | 100 | 100 |
| 17 | 59.2 | 13.3 | 23.4 | 100 | 100 | 100 |
| 18 | 59.2 | 9.0 | 17.0 | 100 | 100 | 100 |
| 19 | 60.0 | 2.4 | 6.1 | 100 | 100 | 100 |
| 20 | 59.0 | 6.6 | 18.4 | 100 | 100 | 100 |
| 21 | 57.0 | 5.8 | 9.5 | 100 | 100 | 100 |
| 22 | 60.0 | 98 | 98 | 86 | 86 | 98 |
| 23 | 61.3 | 76 | 88 | 98 | 98 | 98 |

The in vivo efficacy of the coating compositions according to the invention may be demonstrated in the following test:

Samples (approximately 0.5 g) of coated granules are introduced into nylon bags with a mesh size of 300×300 microns. The bags are placed for 48 hours in the rumen of fistulated ewes. The bags are then recovered and washed. 3 or 4 ewes are used per product. The quantity of active substance present in the bags is determined by a suitable method.

The results obtained are collated in table 3.

TABLE 3

| Examples | | Active substance | Stearic acid/ copolymer ratio | % Active substance extracted after 48 h |
|---|---|---|---|---|
| 1 | A | Methionine | 80/20 | 5 |
| | B | | | 0 |
| | C | | | 0 |
| 5 | I | Lysine hydrochloride | 80/20 | 11 |
| | J | | | 1 |
| | K | | | 7 |
| | L | | | 2 |
| 6 | M | Lysine hydrochloride | 85/15 | 0 |
| | N | | | 0 |
| | O | | | 11 |
| | P | | | 5 |

EXAMPLE 24

According to the "spray-coating" technique, granules (350 g) containing vitamin A acetate, the diameter of which is between 0.5 and 0.8 mm and the composition by weight of which is as follows:
vitamin A acetate: 32.2%
gelatin: 40.9%
lactose: 9.2%
glycerine: 6.6%
stabilizers: 11.1%
are coated with a coating solution with the following composition:

stearic acid (PRIFRAC 9553): 114.8 g
2-vinylpyridine/styrene (70:30) copolymer: 28.7 g
ethanol: 650 cc
1,2-dichloroethane: 650 cc The solution, maintained at 36° C., is sprayed at a rate of 10 cc/minute.

Coated granules, the concentration of which, expressed as vitamin A, is 618,000 IU/g are thus obtained, the starting granules having a concentration of 845,000 IU/g.

The in vitro release is determined at 37° C. in an artificial gastric medium with a pH of 1.2 in the presence of pepsin (according to USP XX).

After 2 hours, the percentage of active product released is 93% for the coated granules and 86% for the starting granules.

After 48 hours, the resistance to rumen conditions is 86.0±3.2% for the coated granules and 3.0±2.2% for the starting granules.

We claim:

1. A composition suitable for coating a biologically active substance to be fed to a ruminant, the said composition being stable in a medium with a pH greater than or equal to 5 and enabling the biologically active substance to be released in a medium with a pH less than 3.5, which composition consists essentially of a basic amino copolymer of one or more vinylpyridines with styrene in which the nitrogen content is from 3 to 14% by weight of said copolymer and a hydrophobic substance having a melting point greater than 60° C. selected from fatty acids, fatty esters, fatty alcohols and mixtures thereof, the hydrophobic substance content being from 55 to 90% of the total weight of the said composition.

2. A composition according to claim 1, wherein the basic amino copolymer is a copolymer of styrene with one or more of 2-vinylpyridine, 4-vinylpyridine or 2-methyl-5-vinyl-pyridine.

3. A composition according to claim 1, wherein the hydrophobic substance is stearic acid or behenic acid.

4. A composition according to claim 4, wherein the hydrophobic substance is stearic acid with a purity greater than 90%.

5. A composition according to claim 1, which additionally contains one or more adjuvant which is an antistatic agent, fungicide, emulsifier, compatibility-inducing agent, cellulose ether, inorganic salt, starch or protein, the adjuvant or adjuvants representing three percent or less by weight of the coating composition.

6. A granule suitable for oral administration to animals, comprising a nucleus comprising a biologically active substance, surrounded by a coating composition according to claim 1.

7. A granule according to claim 6, wherein the coating composition represents from 5 to 50% by weight of the coated granule.

8. A granule according to claim 6, wherein the active substance is a medicinal compound, hormone, vitamin or amino acid.

9. A granule according to claim 6, wherein the active substance is methionine or lysine.

* * * * *